United States Patent [19]

Murtha et al.

[11] 4,268,699
[45] May 19, 1981

[54] HYDROALKYLATION USING NICKEL-RUTHENIUM CATALYST ON ZEOLITE TYPE SUPPORT

[75] Inventors: Timothy P. Murtha; Ernest A. Zuech, both of Bartlesville, Okla.

[73] Assignee: Phillips Petroleum Company, Bartlesville, Okla.

[21] Appl. No.: 101,378

[22] Filed: Dec. 7, 1979

Related U.S. Application Data

[62] Division of Ser. No. 926,601, Jul. 21, 1978, abandoned.

[51] Int. Cl.³ .......................... C07C 5/03; C07C 5/10
[52] U.S. Cl. ................................. 585/268; 585/270; 585/427
[58] Field of Search .................... 585/268, 467, 427

[56] References Cited

U.S. PATENT DOCUMENTS

| | | | |
|---|---|---|---|
| 2,971,904 | 2/1961 | Gladrow et al. | 252/455 Z |
| 3,140,252 | 7/1964 | Frilette et al. | 252/455 Z |
| 3,342,725 | 9/1967 | Young | 252/455 Z |
| 3,412,165 | 11/1968 | Slaugh et al. | 585/268 |
| 3,437,586 | 4/1969 | Weiss | 585/419 |
| 3,496,246 | 2/1970 | Chen | 252/455 Z |
| 3,503,871 | 3/1970 | Gladrow et al. | 208/111 |
| 3,686,121 | 8/1972 | Kimberlin et al. | 252/455 Z |
| 3,706,694 | 12/1972 | Young | 252/455 Z |
| 3,770,845 | 11/1973 | Hirschler | 585/739 |
| 3,829,514 | 8/1974 | Zeuch | 585/268 |
| 3,829,515 | 8/1974 | Zeuch et al. | 585/268 |
| 4,118,434 | 10/1978 | Murtha et al. | 585/268 |
| 4,122,125 | 10/1978 | Murtha et al. | 585/268 |

*Primary Examiner*—Curtis R. Davis

[57] ABSTRACT

Hydroalkylation of aromatic hydrocarbons using an acidic crystalline zeolite type support having ruthenium and nickel thereon, the nickel having been placed thereon responsive to correlation of hydroalkylation selectivity and the amount of alkali metal or alkaline earth metal ion removed from the support during cation exchange when preparing a catalyst. In one embodiment benzene is converted to cyclohexylbenzene.

8 Claims, No Drawings

HYDROALKYLATION USING NICKEL-RUTHENIUM CATALYST ON ZEOLITE TYPE SUPPORT

This is a division of Ser. No. 926,601, filed July 21, 1978 and now abandoned. This invention relates to hydroalkylation. In one of its aspects it relates to an improved hydroalkylation of an aromatic with such a catalyst having improved hydroalkylation selectivity.

In one of its concepts the invention provides a hydroalkylation process for the conversion of an aromatic to a cycloalkyl aromatic using an acidic crystalline zeolite type catalyst support having ruthenium and nickel thereon, the nickel being supplied by nickel chloride to a predominantly alkali metal aluminosilicate support when the alkali metal to aluminum ratio is in the approximate range 0/1 to 0.182/1 and to a predominantly alkaline earth metal aluminosilicate support when the alkaline earth metal to aluminum ratio is in the approximate range 0/1 to 0.091/1; and by nickel bromide when the support is predominantly an alkali metal or alkaline earth metal aluminosilicate support and said ratios are respectively 0.182/1 to 0.4/1 and 0.091/1 to 0.2/1; and wherein ruthenium is added to the support after the calcination.

Aromatic hydrocarbons can be converted to cycloalkyl aromatic hydrocarbons in the presence of hydrogen and a suitable catalyst. Such a process has been called hydroalkylation and suitable catalysts for said process are termed hydroalkylation catalysts. The prior art dealing with the hydroalkylation process has suggested that a dual function catalyst is desired to achieve the hydroalkylation reaction. Specifically, the prior art has taught that a suitable hydroalkylation catalyst should possess both hydrogenation activity and alkylation activity which is generally associated with acidity of the catalyst. Furthermore, it has been suggested that a balance between hydrogenation activity and alkylation activity of the catalyst should be achieved in order to obtain high yields of the cycloalkyl aromatic hydrocarbons. Otherwise, when hydrogenation activity predominates, the process will produce predominately cycloalkanes or when alkylation activity predominates, higher molecular weight multialkylated products can predominate. It is thus apparent that the discovery of hydroalkylation catalysts with good selectivity to the desired cycloalkyl aromatic hydrocarbon is a difficult yet extremely important factor in this area.

U.S. Pat. No. 3,829,515, Aug. 13, 1974, E. A. Zeuch, M. M. Johnson and G. P. Nowack sets forth a process for producing cycloalkylaromatics and alkyl-substituted cycloalkylaromatics by contacting a monocyclic aromatic hydrocarbon or alkyl-substituted monocyclic aromatic hydrocarbon with hydrogen in the presence of a ruthenium halide-active clay catalyst comprising ruthenium promoted with at least one compound of iron, cobalt, and nickel under conditions sufficient to substantially convert said monocyclic aromatic hydrocarbons to cycloalkyl-aromatics and alkyl-substituted cycloalkylaromatic hydrocarbons. The disclosure of the patent is incorporated herein by reference.

Broadly, the instant invention provides a process for the hydroalkylation conversion of aromatic hydrocarbons to cycloalkyl aromatic hydrocarbons. Further, it provides a method of improving the selectivity and/or activity of said catalyst to the cycloalkyl aromatic hydrocarbons.

The hydroalkylation catalyst of the process of the instant invention can be broadly described as a catalyst of ruthenium/nickel on an acidic type X or type Y crystalline zeolite (molecular sieve) support.

According to the present invention the improvement in selectivity to or yield of the cycloalkyl aromatic hydrocarbon product obtained with the above hydroalkylation catalyst is achieved, broadly speaking, by matching or correlating the nickel compound source with the extent of alkali metal (sodium) or alkaline earth metal removal from the crystalline zeolite support.

The nickel compound sources, i.e., the nickel chloride and nickel bromide, are, according to the invention, matched by observing the following selection rules as one manner of preparing the catalyst.

Nickel Chloride

When the alkali metal to aluminum ratio of the aluminosilicate (zeolite) support is in the approximate range 0/1 to 0.182/1 nickel chloride is selected.

Or, also when the alkaline earth metal/aluminum ratio of the aluminosilicate (zeolite) support is in the approximate range 0/1 to 0.091/1 nickel chloride is selected.

Nickel Bromide

When the alkali metal/aluminum ratio of the aluminosilicate (zeolite) support is in the approximate range 0.182/1 to 0.4/1 or when the alkaline earth metal/aluminum ratio of the aluminosilicate (zeolite) support is in the approximate range 0.091/1 to 0.2/1 nickel bromide is selected.

It is an object of this invention to provide an improved process for hydroalkylation of an aromatic using a hydroalkylation catalyst. It is another object of this invention to provide a method for the determination of nickel source for a ruthenium and nickel containing catalyst.

Other aspects, concepts, objects and the several advantages of this invention are apparent from a study of this disclosure and the appended claims.

According to the present invention there is provided a process for the hydroalkylation of an aromatic compound, e.g., benzene, by subjecting it to hydroalkylation conditions in the presence of a catalyst comprising an acidic crystalline zeolite type support having a substantial proportion of crystalline zeolitic component therein said support having been prepared by removing alkali metal or alkaline earth metal ions by cation exchange treatment with an ammonium compound followed by calcination to convert ammonium ions to protonic acidic sites, said support having thereon ruthenium and nickel, the nickel being supplied by nickel chloride to a predominantly alkali metal cation exchanged aluminosilicate support when the alkali metal to aluminum ratio is in the approximate range 0/1 to 0.182/1 and to a predominantly alkaline earth metal cation exchanged aluminosilicate support when the alkaline earth metal to aluminum ratio is in the approximate range 0/1 to 0.091/1; and by nickel bromide when the support is predominantly a cation exchanged alkali metal or alkaline earth metal aluminosilicate support and said ratios are respectively 0.182/1 to 0.4/1 and 0.091/1 to 0.2/1; and wherein ruthenium is added to the support after the calcination.

Still according to the invention the preferred support is prepared using a crystalline alkali metal aluminosilicate, e.g., a suitable molecular sieve.

Also according to the invention the nickel source for a hydroalkylation catalyst, as described herein, is determined by correlating the hydroalkylation selectivity of the catalyst and the amount of sodium removed from the support.

The support material for the catalyst of the instant invention is a crystalline zeolite of type X or type Y in either alkali metal or alkaline earth metal form which has been treated under cation exchange conditions with ammonium compounds or a mixture of ammonium compounds and nickel compounds. The crystalline zeolites are sometimes called molecular sieves because of the essentially uniform pore diameters in these crystalline alkali metal aluminosilicates. Type Y synthetic crystalline zeolites are described, for example, in U.S. Pat. No. 3,130,007. Such materials are presently commercially available as for example molecular sieve SK-40 from the Linde Division of Union Carbide Corporation. The support of the catalyst of the invention preferably will contain a substantial proportion of crystalline zeolite component. Though not now preferred, there should be at least about 35% of such component in the support. Presently, the support will be prepared using a crystalline alkali metal aluminosilicate, e.g., a molecular sieve. These materials are crystalline and have been used in obtaining the data given herein.

The alkaline earth metal or alkali metal (usually sodium) form of the above synthetic crystalline zeolite is treated under cation-exchange conditions with ammonium compounds or a mixture of ammonium compounds and nickel compounds in order to provide the suitable support material for use in preparation of the catalyst of this invention.

The cation-exchange process is a well-known conventional procedure in order to remove the alkali metal (sodium) or alkaline earth metal cations and replace said cations with ammonium ions or a mixture of ammonium ions and nickel ions. Upon subsequent calcination of this material, the ammonium ions are converted to protonic acid sites on the catalyst, thus providing acidic character to this catalyst material. In terms of a batch cation-exchange process, it is estimated that one exchange treatment removes 60% of the sodium while two exchange steps remove about 70-71% of the sodium and three exchange steps remove about 82% of the sodium.

It has been found, according to the instant invention, on the one hand, that improved catalyst performance in the hydroalkylation reaction in terms of yield of the desired cycloalkyl aromatic compound is achieved when nickel chloride is utilized as a source of nickel in the situation wherein three cation-exchange steps have been carried out on the catalyst support or, in other words, about 80-82% of the sodium has been exchanged. On the other hand, an improvement in terms of selectivity to the cycloalkyl aromatic compound is achieved when nickel bromide is utilized as a source of nickel in the instance wherein the support material has been cation-exchanged with two steps or, in other words, wherein about 70-71% of the sodium has been exchanged. The explanation for this correlation between catalyst selectivity and/or activity and the source of the nickel compound is not known at present.

As indicated above, the nickel component of the hydroalkylation catalyst can be added to the catalyst support during the cation-exchange steps. The nickel component can also be added to the support subsequent to the cation-exchange process either before or after the support material has been calcined. If the nickel compound is added after the support has been calcined, the addition can be carried out in admixture with the ruthenium component or in a separate step therefrom.

The impregnation of the catalyst support material with the nickel component or admixture thereof with the ruthenium component is carried out under total impregnation conditions. The nickel and/or ruthenium compound, in a suitable solvent or diluent, is added to the calcined catalyst support and the solvent or diluent, completely evaporated. Under such conditions, the catalyst is then ready for use in the hydroalkylation process.

The addition of the ruthenium component is carried out by adding a solution or dispersion of a suitable ruthenium compound to the previously calcined support material followed by evaporation of the solvent or diluent to provide the catalyst suitable for use in the hydroalkylation process. In any case, the catalyst support, with or without the nickel component, is calcined prior to the addition or ruthenium component regardless of when it is added. The ruthenium component added to the catalyst support as described above is a ruthenium halide, preferably ruthenium trichloride because of its ready availability.

The amount of nickel in the final catalyst composite is broadly within the range of from about 0.001 to about 5 and preferably from about 0.01 to about 1% be weight in order to achieve a reasonable balance between catalyst activity and cost thereof.

The amount of ruthenium is broadly within the range from about 0.001 to about 5 and preferably from about 0.01 to about 1% be weight also in order to achieve a reasonable balance between catalyst activity and cost.

One skilled in the art in possession of this disclosure, having studied the same, can determine by routine test the optimum ratio of nickel to ruthenium for his purposes.

The catalyst described above is employed for the hydroalkylation of aromatic hydrocarbon to produce cycloalkyl aromatic hydrocarbons. The feedstocks which are suitable for use in the present invention are aromatic compounds, i.e., monocyclic aromatic hydrocarbons and alkyl-substituted monocyclic aromatic hydrocarbons. Some specific examples of these are benzene, toluene, xylenes and the like, and mixtures thereof. The aromatic hydrocarbon feed should be essentially free of sulfur compounds and other known hydrogenation catalyst poisons.

The process of the invention using the catalyst described is particularly valuable for the conversion of benzene to cyclohexylbenzene. Cyclohexylbenzene is known as a valuable solvent and chemical intermediate. It can be converted in high yield to phenol and cyclohexanone via autooxidation to the corresponding hydroperoxide followed by subsequent acid treatment of the hydroperoxide. It is also useful as an intermediate in the production of cyclohexene which in turn can be utilized for the production of adipic acid and caprolactam.

The aromatic hydrocarbon feedstock is fed to the catalyst in the reaction zone at a liquid hourly space velocity (LHSV) of from 1 up to 100 and preferably from 5 up to 30 in order to obtain a reasonable balance between feedstock conversion and selectivity to the desired product. The reaction is carried out under a hydrogen pressure of from 690 to $13.8 \times 10^3$ kPa (100–2000 psig) and preferably from 1380 up to 6900 kPa (200–1000 psig). Furthermore, the hydrogen feed rate to the reaction zone is broadly within the range of from 0.1 up to 10 moles of hydrogen per mole of aromatic hydrocarbon feed per hour and preferably from 0.2 up to 1 mole per mole of feed per hour.

The temperature employed in the hydroalkylation reaction zone is broadly from 100° up to 250° C. and preferably from 150° up to 210° C.

The hydroalkylation reaction is conveniently carried out by having the above described catalyst in a fixed bed and then contacting said catalyst with the aromatic hydrocarbon feed and hydrogen in an upflow or downflow arrangement. It is also possible to employ a countercurrent flow of hydrogen and the aromatic hydrocarbon feed over the catalyst in the reaction zone. It is also possible, though less preferred, to utilize a batch process for the hydroalkylation reaction.

Although not absolutely necessary, it is preferred that the hydroalkylation catalyst undergo a prereduction under hydrogen prior to the introduction of the aromatic hydrocarbon feed in the hydroalkylation process. Such a prereduction is generally carried out for about 15 minutes to one hour under a stream of flowing hydrogen at a temperature of about 150°–175° C. and at a hydrogen pressure of about 3,450 kPa (500 psig).

The effluent from the reaction zone can be conveniently separated into the desired reaction product and unreacted feed and by-products by fractional distillation procedures. Unreacted feed and hydrogen can be recycled to the reaction zone as desired.

EXAMPLES

In the hydroalkylation runs of the following Examples, the reaction system that was utilized consisted of a tubular reaction vessel which was charged with the catalyst in the amounts indicated. On some occasions, the catalyst bed was placed in the reaction vessel between two layers of small glass beads. The reaction system was equipped for continuous operation with suitable means for heating the reaction zone and for sampling the reaction zone effluent for analysis by gas-liquid phase chromatography.

EXAMPLE I

The runs of this Example are control runs in that the hydroalkylation catalyst (no. 1) utilized was prepared by impregnation of a type Y crystalline zeolite support (Linde SK-40 mole sieves) with ruthenium trichloride and nickel chloride but wherein the support had not been cation-exchanged with an ammonium compound and then calcined to provide acidic sites on the support material. This catalyst was prepared by using a solution of 0.203 grams of nickel chloride hexahydrate and 0.0615 grams of ruthenium trichloride in absolute ethanol to impregnate 25 grams of the type Y crystalline zeolite support. The solvent was evaporated and the catalyst, 15 ml (10.0 g), then charged to the reaction zone in the continuous reaction system described above. The catalyst thus prepared contained 0.1 weight % ruthenium and 0.2 weight % nickel. The catalyst was prereduced at 150° C. under 500 psig hydrogen pressure for 15 minutes and at a hydrogen flow rate of 0.5 liter per minute. Benzene feed was then charged to the reaction zone at the rate indicated in Table 1 below. The results obtained with the above described catalyst in two hydroalkylation runs are given below in Table 1. Other conditions utilized in the hydroalkylation runs are also presented in Table 1.

TABLE I

| Run No. | Temp °C. | Benzene LHSV | Benzene Conv. % | Selectivity Wt. %[a] CH[b] | Selectivity Wt. %[a] CHB[c] | Weight Ratio CHB/CH |
|---|---|---|---|---|---|---|
| 1 | 250 | 8 | 23.8 | 97.8 | 0.02 | — |
| 2 | 190 | 20 | 4.8 | 100.0 | — | — |

[a]Analysis by gas-liquid phase chromatography (GLC) of reaction zone effluent
[b]CH = Cyclohexane
[c]CHB = Cyclohexylbenzene It is evident from the results of Table I that catalyst No. 1 possessed very little selectivity for the desired product, cyclohexylbenzene. This catalyst under the conditions utilized tended to give almost exclusively hydrogenation of the benzene feed to cyclohexane.

EXAMPLE II

Catalyst No. 2 utilized in the instant Example was prepared by a two-step exchange process wherein ammonium chloride was utilized to carry out a cation-exchange of the type Y crystalline zeolite.

The cation-exchange process was carried out by heating 200 grams of Linde SK-40 mole sieves 20–30 mesh with a solution of 242 grams of $NH_4Cl$ in 2,000 ml of deionized water to 100° C. for about three hours. The hot mixture was filtered and the zeolite washed with water. The zeolite was then treated with another solution of $NH_4Cl$ under essentially the same conditions, filtered, washed with water and dried overnight to remove excess wash water.

The zeolite material obtained after the two-step cation-exchange process was calcined by heating the material slowly over a four hour period to 583° C. (1000° F.) and then holding the temperature at that level for an additional two hours. The sample was allowed to cool in ambient air and was placed in a sample storage bottle. A portion (9.0 grams) of the above described calcined support material was with a solution of 0.0221 grams of ruthenium trichloride and 0.0727 grams of nickel chloride hexahydrate in about 20 ml of absolute ethanol. The catalyst was air dried overnight to remove the ethanol and then placed in a sample bottle.

Catalyst No. 3 was also prepared by a two-step cation-exchange process on the same type Y crystalline zeolite support. In this instance, the two-step cation-exchange process was carried out by heating 100 grams of the zeolite with a solution of 120.5 grams of $NH_4Cl$ in one liter of deionized water for about 2 hours of about 90° C. The hot mixture was filtered and the zeolite heated again with another one liter solution of 120.5 grams of $NH_4Cl$ for about 2 hours at 100° C. The mixture was again filtered and the solid washed with about 500 ml of deionized water. The solid material was then ground to provide about 30 ml of 20–30 mesh material.

The cation-exchanged crystalline zeolite obtained as described above was calcined by heating the support material from 90° C. to 550° C. over a four hour period. The material was allowed to cool overnight and then placed in an oven and heated at 510° C. for two hours. The material was allowed to cool again and stored in a sealed sample bottle. A portion (20 grams) of the above described calcined support was sprayed with a solution of 0.0248 grams of ruthenium trichloride and 0.2776 grams of nickel bromide trihydrate in about 20 ml of ethanol and 1 ml of water. The resulting impregnated catalyst was allowed to dry in the air for about 30 minutes and then sealed in a sample bottle.

Catalyst No. 2 prepared as described above contained 0.1 weight percent ruthenium and 0.2 weight percent nickel while catalyst No. 3 contained 0.05 weight percent ruthenium and 0.3 weight percent nickel.

In the hydroalkylation runs using catalysts 2 and 3, the reactor was charged with 10 ml of the catalyst in each instance. Catalyst No. 2 (6.8 g) was prereduced by heating the catalyst in the reaction zone to 150° C. at 500 psig hydrogen pressure and a flow rate of hydrogen through the system of 0.5 liters per minute for a period of 30 minutes. Catalyst No. 3 (7.2 g) was prereduced under essentially the same conditions with the exception that the prereduction period was for 15 minutes rather than 30 minutes for catalyst No. 2.

Results obtained in benzene hydroalkylation to cyclohexylbenzene with catalysts 2 and 3 are presented in Table II below along with other reaction conditions utilized in the hydroalkylation runs with the above catalysts.

TABLE II

| Run No. | Temp. °C. | Benzene LHSV | Conv. % | Selectivity, Wt. % CH | CHB | Weight Ratio CHB/CH |
|---|---|---|---|---|---|---|
| 3[a] | 180 | 25 | 9.8 | 24.5 | 68.4 | 2.8 |
| 4[a] | 208 | 10 | 18.3 | 23.5 | 69.9 | 3.0 |
| 5[b] | 190 | 15 | 5.7 | 7.7 | 80.6 | 10.5 |
| 6[b] | 210 | 30 | 7.6 | 7.9 | 80.2 | 10.1 |

[a]Catalyst No. 2.
[b]Catalyst No. 3.

The results of Table II demonstrate that a much better selectivity to cyclohexylbenzene was obtained when the source of nickel was nickel bromide in the preparation of the catalyst having two-step cation-exchange procedure of the type Y zeolite than when the source of nickel was nickel chloride.

EXAMPLE III

The catalysts utilized in the hydroalkylation runs of this Example were prepared from a type Y crystalline zeolite of the kind previously used (Linde SK-40) but wherein the cation-exchanged process was carried out in a three-step operation rather than the two-step procedure described in Example II above. The three-step cation-exchange treatment was performed in essentially the same manner as that given for the two-step treatment but simply with the additional or third step being utilized in the cation-exchange treatment. The cation-exchange zeolite support was calcined in essentially the same manner used for catalyst No. 2 and was then impregnated with solutions of ruthenium trichloride and nickel chloride for catalyst No. 4 and mixtures of ruthenium trichloride and nickel bromide for catalysts 5 and 6. Said impregnation treatment with the mixtures of ruthenium and nickel compounds was carried out under total impregnation conditions previously described. The catalysts thus prepared had the following composition: Catalyst No. 4, 0.10 weight percent ruthenium, 0.10 weight percent nickel; catalyst No. 5, 0.10 weight percent ruthenium, 0.10 weight percent nickel and catalyst No. 6, 0.05 weight percent ruthenium and 0.20 weight percent nickel.

The hydroalkylation runs utilizing these catalysts were carried out in the continuous reaction system previously described. The catalysts were prereduced under conditions similar to those described earlier prior to the introduction of benzene feed into the reaction zone. The results obtained in these hydroalkylation runs, as well as the other reaction conditions utilized therein, are presented below in Table III.

TABLE III

| Run No. | Temp. °C. | Benzene LHSV | Conv. % | Selectivity, Wt. % CH | CHB | Weight Ratio CHB/CH |
|---|---|---|---|---|---|---|
| 7[a] | 180 | 20 | 14.7 | 17.2 | 73.8 | 4.3 |
| 8[a] | 200 | 15 | 16.7 | 15.6 | 73.0 | 4.7 |
| 9[b] | 210 | 10 | 0.2 | — | — | — |
| 10[c] | 230 | 10.6 | trace | — | — | — |

[a]Catalyst No. 4.
[b]Catalyst No. 5.
[c]Catalyst No. 6.

The results shown in Table III demonstrate that when the type Y crystalline zeolite has been subjected to a three-step cation-exchange process, thus providing a support material of lower sodium content than the two-step cation-exchange procedure, that nickel chloride provides a much more active catalyst for the hydroalkylation process than nickel bromide.

One skilled in the art in possession of this disclosure, having studied the same, can determine by routing testing the optimum treatment of the catalyst support, e.g., the matching of the nickel compound source with the extent of alkali metal removal, as described or however effected. Also, one skilled in the art will recognize that there has been set forth a modus operandi whereby the nickel source for a hydroalkylation catalyst, as herein described, can be selected by correlating the hydroalkylation selectivity of the final catalyst and the amount of sodium ion removed from the support. Reasonable variation and modification are possible within the scope of the foregoing disclosure and the appended claims to the invention the essence of which is that a process for hydroalkylating an aromatic with a hydroalkylation catalyst comprising nickel and ruthenium on an acidic crystalline zeolite type support and having certain predetermined source of nickel, i.e., nickel chloride or nickel bromide, depending upon the hydroalkylation selectivity of the final catalyst and the amount of alkali metal or alkaline earth metal removed from the support by cation exchange during the preparation of the catalyst has been set forth as described.

We claim:

1. A process for the hydroalkylation of an aromatic compound which comprises subjecting it to hydroalkylation conditions in the presence of a catalyst comprising an acidic crystalline zeolite type support having a substantial proportion of crystalline zeolitic component therein, said support having been prepared by removing alkali metal or aklaline earth metal ions by cation exchange treatment with an ammonium compound followed by calcination to convert ammonium ions to protonic acid sites, said support having thereon ruthenium and nickel, the nickel being supplied by nickel chloride to a predominantly alkali metal cation exchanged aluminosilicate support when the alkali metal to aluminum ratio is in the approximate range 0/1 to 0.182/1 and to a predominantly alkaline earth metal cation exchanged aluminosilicate support when the alkaline earth metal to aluminum ratio is in the approximate range 0/1 to 0.091/1; and by nickel bromide when the support is predominantly a cation exchanged alkali metal or alkaline earth metal support and said ratios are respectively 0.182/1 to 0.4/1 and 0.091/1 to 0.2/1; and wherein ruthenium is added to the support after the calcination.

2. A process according to claim 1 wherein the aromatic compound is selected from monocyclic- and alkyl-substituted monocyclic aromatic compounds.

3. A process according to claim 2 wherein the compound is at least one selected from benzene, toluene, and a xylene.

4. A process according to claim 1 wherein the support contains at least about 35% of crystalline zeolite component.

5. A process according to claim 1 wherein the support is prepared using a crystalline alkali metal aluminosilicate.

6. A process according to claim 1 wherein the support is prepared using a suitable molecular sieve.

7. A process according to claim 1 wherein the amounts of each of the nickel and ruthenium in the final catalyst composite is in the range of from about 0.001 to about 5% by weight.

8. A process according to claim 1 wherein the amounts of each of the nickel and ruthenium in the final catalyst composite is in the range of from about 0.01 to about 1% by weight.

* * * * *